(12) United States Patent
Lee et al.

(10) Patent No.: US 10,494,637 B2
(45) Date of Patent: Dec. 3, 2019

(54) MUTANT HAVING ABILITY TO OVERPRODUCE CAROTENOIDS AND METHOD FOR PRODUCING CAROTENOIDS BY USING SAME

(71) Applicant: AJOU UNIVERSITY INDUSTRY-ACADEMIC COOPERATION FOUNDATION, Suwon-si, Gyeonggi-do (KR)

(72) Inventors: Pyung Cheon Lee, Yongin-si (KR); Bo Hyun Choi, Mokpo-si (KR); Sun Hyoung Choi, Seoul (KR)

(73) Assignee: AJOU UNIVERSITY INDUSTRY-ACADEMIC COOPERATION FOUNDATION, Suwon-si, Gyeonggi-do (KR)

( * ) Notice: Subject to any disclaimer, the term of this patent is extended or adjusted under 35 U.S.C. 154(b) by 104 days.

(21) Appl. No.: 15/540,611

(22) PCT Filed: Dec. 31, 2015

(86) PCT No.: PCT/KR2015/014558
§ 371 (c)(1),
(2) Date: Oct. 31, 2017

(87) PCT Pub. No.: WO2016/108662
PCT Pub. Date: Jul. 7, 2016

(65) Prior Publication Data
US 2018/0148728 A1  May 31, 2018

(30) Foreign Application Priority Data

Dec. 31, 2014 (KR) .................. 10-2014-0194792

(51) Int. Cl.
*C12N 15/70* (2006.01)
*C12P 23/00* (2006.01)
*C12N 15/01* (2006.01)
*C12N 9/02* (2006.01)
*C12N 9/10* (2006.01)
*C12N 9/90* (2006.01)

(52) U.S. Cl.
CPC ............ *C12N 15/70* (2013.01); *C12N 9/001* (2013.01); *C12N 9/0073* (2013.01); *C12N 9/1048* (2013.01); *C12N 9/1085* (2013.01); *C12N 9/90* (2013.01); *C12N 15/01* (2013.01); *C12P 23/00* (2013.01); *C12Y 103/9903* (2013.01); *C12Y 114/13129* (2013.01); *C12Y 205/01001* (2013.01); *C12Y 205/01032* (2013.01); *C12Y 505/01019* (2013.01)

(58) Field of Classification Search
None
See application file for complete search history.

(56) References Cited

U.S. PATENT DOCUMENTS

2004/0146966 A1  7/2004  Cheng et al.
2005/0014219 A1  1/2005  Cheng et al.

OTHER PUBLICATIONS

NCBI, GenBank accession No. JX871355.1 (Jan. 2, 2013).
NCBI, GenBank accession No. JX871356.1 (Jan. 2, 2013).
NCBI, GenBank accession No. JX871357.1 (Jan. 2, 2013).
NCBI, GenBank accession No. JX871358.1 (Jan. 2, 2013).
NCBI, GenBank accession No. JX871360.1 (Nov. 21, 2012).
NCBI, GenBank accession No. JX871359.1 (Jan. 2, 2013).

*Primary Examiner* — Jennifer E Graser
(74) *Attorney, Agent, or Firm* — Vorys, Sater, Seymour & Pease LLP; Mih Suhn Koh (57) ABSTRACT

Provided is a mutant having an ability to overproduce carotenoids and a method for producing carotenoids by using the mutant. The mutant, of which mutations are induced by irradiation after being transformed with a recombinant vector according to the subject matter, has an excellent ability to produce carotenoids and can be mass-produced, and thus can be useful in various industrial fields, which use carotenoids, such as cosmetics, food, and feed.

5 Claims, 5 Drawing Sheets
Specification includes a Sequence Listing.

MUTANT HAVING ABILITY TO OVERPRODUCE CAROTENOIDS AND METHOD FOR PRODUCING CAROTENOIDS BY USING SAME

SEQUENCE LISTING

The Sequence Listing submitted in text format (.txt) filed on Nov. 17, 2017, named "SequenceListing.txt", created on Nov. 17, 2017, 11.2 KB), is incorporated herein by reference.

TECHNICAL FIELD

The present invention relates to a mutant strain having an ability to over-produce carotenoids and a method for producing carotenoids using the mutant strain.

BACKGROUND ART

Carotenoids are $C_{40}$ isoprenoid compounds having antioxidant activity, such as astaxanthin (exists in salmons and sea lobsters), lycopene (red pigment of tomatoes), and fucoxanthin (yellowish brown or brown pigment of seaweeds). The carotenoids act as precursors of vitamin A in the body and are known to have excellent antioxidant effect, harmful oxygen scavenging action, cancer cell proliferation inhibitory action, and carcinostatic action, so as to prevent circulatory diseases, cancers, adult diseases, and the like. Beta-carotene acts as a precursor of vitamin A in the body and is known to have strong antioxidant effect, harmful oxygen scavenging action, cancer cell proliferation inhibitory action, and carcinostatic action, thereby preventing circulatory diseases, cancers, adult diseases, and the like. Recently, carotenoids have begun to become popular cosmetic ingredients in Europe and the United States, as it has been exhibited that carotenoids directly enhance the body's immune function by ultraviolet rays so as to reduce skin damage from exposure to ultraviolet rays or to inhibit melanin production. Currently, carotenoids are used as health food ingredients (nutritional supplements), pharmaceutical preparations for human, food coloring agents, animal feed pigments, or the like.

The carotenoid biosynthetic pathway is derived from farnesyl pyrophosphate (FPP), an important intermediate product of the general isoprenoid pathway. FPP and isopentenyl pyrophosphate (IPP) are converted to lycopene through a series of reactions by geranylgeranyl pyrophosphate synthase encoded by CrtB, phytoene synthase encoded by CrtE, and phytoene desaturase encoded by CrtI, and then converted to beta-carotene through a series of reactions by lycopene cyclase encoded by CrtY.

Accordingly, the present inventors have made efforts to develop a novel method for increasing the production of carotenoids. As a result, the inventors have produced a recombinant vector including a gene derived from *Pantoea agglomerans*. The wild microorganisms which do not produce carotenoids are transformed with the recombinant vector, and then a recombinant mutant strain is produced by irradiation. As a result, the recombinant mutant strain is confirmed to have an ability to over-produce carotenoids, thereby completing the present invention.

DISCLOSURE

Technical Problem

An object of the present invention is to provide a recombinant mutant strain having an ability to over-produce carotenoids.

Another object of the present invention is to provide a method for producing carotenoids using the recombinant mutant strain.

Technical Solution

To address the above-mentioned issues, the present invention provides a mutant strain having an ability to over-produce carotenoids, which is mutagenized by irradiation, wherein the mutant strain includes a CrtE gene encoding geranylgeranyl pyrophosphate synthase; a CrtB gene encoding phytoene synthase; a CrtI gene encoding phytoene desaturase; a CrtY gene encoding lycopene beta cyclase; a CrtX gene encoding glucosyltransferase; and a CrtZ gene encoding beta-carotene hydroxylase, which is transformed with a recombinant vector for production of carotenoids.

Further, the present invention provides a method for producing carotenoids, comprising the steps of: (a) culturing the mutant strain; and (b) isolating and purifying the carotenoids from a culture of the mutant strain of the step (a).

Advantageous Effects

The mutant strain which is transformed with the recombinant vector according to the present invention and then is mutagenized by irradiation can have excellent ability to produce carotenoids. Further, it can be mass-produced and be beneficially used in various industrial fields such as cosmetics, foods, and feeds using carotenoids.

DESCRIPTION OF DRAWINGS

FIG. 8A illustrates a wild type of XL1-Blue strain. FIG. 8B illustrates an XL1-Blue strain into which the plasmid pUC19_CrtEXYIBZ was introduced. FIG. 8C illustrates the mutant strain Ajou_CEM45 (KCTC 12683BP) of the present invention.

FIG. 9A illustrates a wild-type XL1-Blue strain. FIG. 9B illustrates an XL1-Blue strain into which the plasmid pUC19_CrtEXYIBZ was introduced. FIG. 9C is the mutant strain Ajou_CEM45 (KCTC 12683BP) of the present invention.

MODES OF THE INVENTION

Hereinafter, the present invention is described in detail.

The present invention provides a mutant strain having an ability to over-produce carotenoids, which is mutagenized by irradiation, in which the mutant strain comprises a CrtE gene encoding geranylgeranyl pyrophosphate synthase; a CrtB gene encoding phytoene synthase; a CrtI gene encoding phytoene desaturase; a CrtY gene encoding lycopene beta cyclase; a CrtX gene encoding glucosyltransferase; and a CrtZ gene encoding beta-carotene hydroxylase, which is transformed with a recombinant vector for production of carotenoids.

The mutant strain is preferably *Escherichia coli* whose accession number is KCTC 12683BP.

In one example of the present invention, a plasmid pUC19_CrtEXYIBZ is introduced into *Escherichia coli* to result in transformation. Then, the recombinant *Escherichia coli* is irradiated with $^{60}$Co of gamma-ray sources to prepare a mutant strain. Thereafter, mutant strains in which the color concentration is enhanced compared to yellow, an intrinsic expression color of beta-carotene which is one kind of carotenoid, are firstly selected and then subjected to secondary selecting based on the intensity of yellow color expressed in the obtained microbial cells, so as to select the mutant strain of the present invention. This strain is named "Ajou_CEM45", which was deposited on Sep. 23, 2014 with Microorganism Resource Center, Korea Research Institute of Bioscience and Biotechnology in Korea, and its accession number is KCTC 12683BP.

The term "vector" in the present invention means a gene product including a nucleotide sequence of a gene operably linked to a suitable regulatory sequence in order to express a target gene in a suitable host, in which the regulatory sequence may include a promoter which can initiate the transcription, any operator sequence which modulates such transcription, and a sequence which regulates the termination of transcription and translation.

The term "operably linked" refers to a functional linkage between a nucleic acid expression control sequence and a nucleic acid sequence encoding a desired protein to perform a general function. For example, nucleic acid sequences encoding a promoter and a protein or RNA may be operably linked to affect the expression of the coding sequence. Operational linkage with a recombinant vector can be made using recombinant DNA techniques well known in the art, and site-specific DNA cleavage and linkage are made using enzymes generally known in the art.

The phrase "expression of the target gene" may mean expression of the target gene to produce a protein encoded by the target gene. In the present invention, a method of expressing a target gene may be a method of expressing a protein encoded by the target gene by culturing a transformant (host cell) transformed with a vector including the target gene. Such a way results in the final product of the biosynthetic pathway in which the protein is involved.

The vector of the present invention is not particularly limited as long as it is replicable in cells, and any vector known in the art may be used such as a plasmid, a cosmid, a phage particle, and a viral vector. For example, the expression vector may be used as a vector commercially available in the art, such as pUC19, pSTV28, pBBR1MCS, pBluscriptII, pBAD, pTrc99A, pET, pACYC 184, and pBR322 families.

The phrase "transformation" in the present invention means that DNA is introduced as a host and the DNA becomes replicable as an extrachromosomal element or by chromosomal integration completion. The transformation includes any method of introducing a nucleic acid molecule into an organism, a cell, tissue, or an organ, and can be carried out by selecting a suitable standard technique depending on the host cell as is known in the art. Such methods may, but be not limited to, include an electroporation, $CaPO_4$ precipitation, $CaCl_2$ precipitation, microinjection, a method using polyethylene glycol (PEG), a method using diethylaminoethyl (DEAE)-dextran, a method using cationic liposome, a method using lithium acetate-DMSO, and the like.

The CrtE gene, the CrtB gene, the CrtI gene, the CrtY gene, the CrtX gene, and the CrtZ gene combination may be such that respective genes constituting the relevant combination are inserted into one vector or are divided into two or more kinds of vectors. Here, when two or more genes are inserted into one vector, the genes may be, but not limited to, inserted in a form having a constitutive promoter (for example, constitutive lac promoter), a terminator, and the like.

The CrtE gene, the CrtB gene, the CrtI gene, the CrtY gene, the CrtX gene, and the CrtZ gene are preferably derived from *Pantoea agglomerans*.

The "*Pantoea agglomerans*" is a gram-negative bacterium belonging to the Enterobacteriaceae family and is known as an opportunistic pathogen that causes a wound, blood, and urinary tract infections. It is found in the surfaces of plants, seeds, fruit, animals, and human excreta.

In the present invention, the CrtE gene, the CrtB gene, the CrtI gene, the CrtY gene, the CrtX gene, and the CrtZ gene can be artificially synthesized using a nucleic acid synthesizer or the like with reference to the nucleotide sequence of the gene, or can be prepared by performing PCR using, as a primer, an oligonucleotide having a sequence complementary to both ends of the target CrtE gene, CrtB gene, CrtI gene, CrtY gene, CrtX gene, and CrtZ gene, in which the organism from which the gene is derived, for example, preferably *Pantaea agglomerans* genomic DNA, is used as a template. Meanwhile, the CrtE gene, the CrtB gene, the CrtI gene, the CrtY gene, the CrtX gene, and the CrtZ gene of the present invention can exist in various nucleotide sequences due to codon degeneracy, all of which are included in the scope of the present invention. Preferably, the CrtE gene may comprise a nucleotide sequence as set forth in SEQ ID NO: 1, the CrtB gene may comprise a nucleotide sequence as set forth in SEQ ID NO: 2, the CrtI gene may comprise a nucleotide sequence as set forth in SEQ ID NO: 3, the CrtY gene may comprise a nucleotide sequence as set forth in SEQ ID NO: 4, the CrtX gene may comprise a nucleotide sequence as set forth in SEQ ID NO: 5, and the CrtZ gene may comprise a nucleotide sequence as set forth in SEQ ID NO: 6. Mutants thereof are included within the scope of the present invention. Specifically, it may include a nucleotide sequence having 70% or more, more preferably 80% or more, still more preferably 90% or more, and most preferably 95% or more of a sequence homology with each of the nucleotide sequences. "% of sequence homology" to polynucleotides is determined by comparing the comparison region with two optimally aligned sequences, and a portion of the polynucleotide sequence in the comparison region can include an addition or a deletion (i.e., gap) compared to the reference sequence (without an addition or a deletion) for the optimal alignment of the two sequences.

Figure 1:
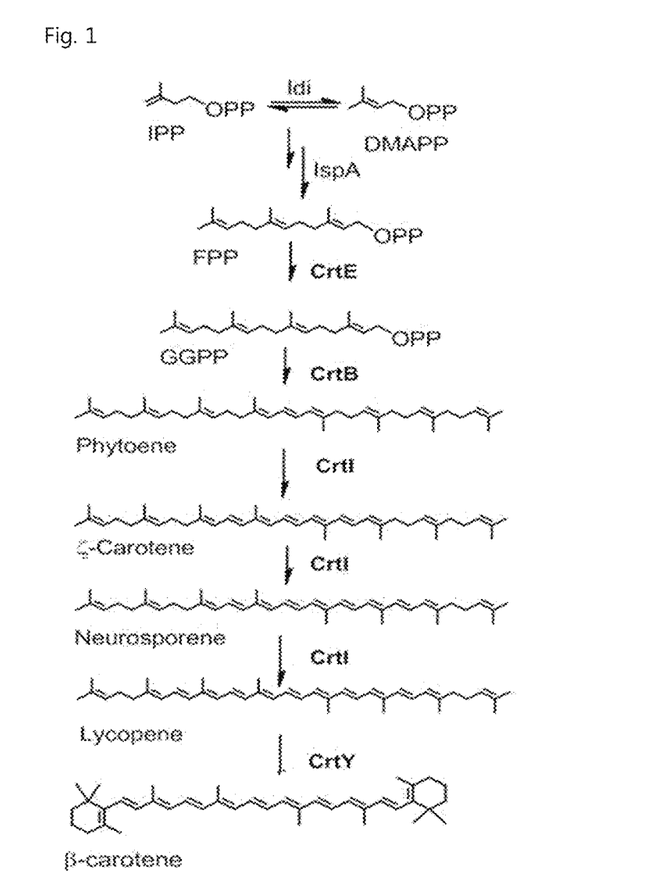
FIG. 1 illustrates schematization of a biosynthetic pathway of carotenoids.
Figure 2:
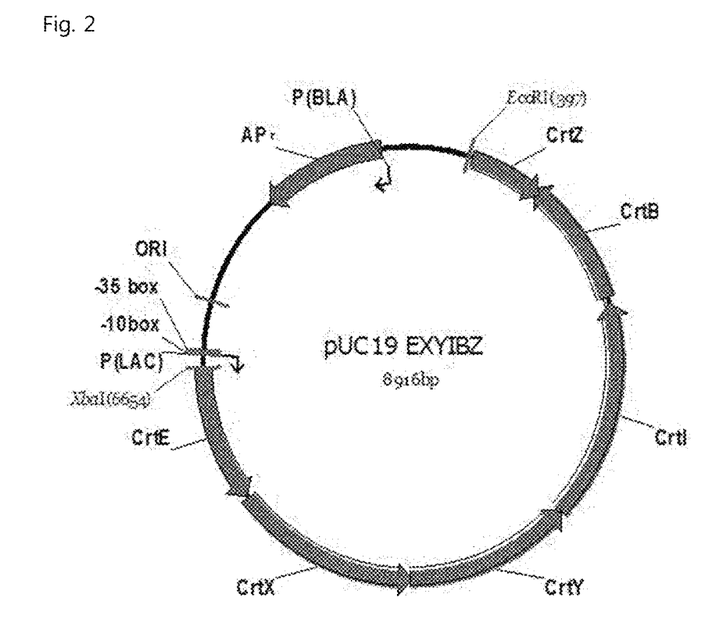
FIG. 2 is a diagram illustrating a vector map of pUC19_CrtEXYIBZ of the present invention.

The recombinant vector for producing carotenoids according to the present invention may, but be not limited to, have the cleavage map, illustrated in FIG. 2.

In the present invention, the irradiation may be performed by irradiating a gamma-ray source having one or more kinds selected from the group consisting of $^{60}$Co, $^{192}$Ir, $^{137}$Cs, and 170Tm, preferably $^{60}$Co, but is not limited thereto.

The radiation may be irradiated at a dose of 0.1 kGy to 3.0 kGy, preferably at a dose of 0.3 kGy to 2.0 kGy, and is sufficient to induce mutation, but is not limited thereto. Further, the radiation can be irradiated for 10 minutes or more, preferably 10 minutes to 60 minutes, and is sufficient to cause mutation, but is not limited thereto.

In the present invention, carotenoids are $C_{40}$ isoprenoid compounds, such as phytoene, neurosporene, β-carotene, lycopene, zeaxanthin, torulene, chlorobactene, flexixanthin, γ-carotene, 4-keto-γ-carotene, myxol, astaxanthin, isorenieratene, canthaxanthin, and nostoxanthin, preferably β-carotene or lycopene, but are not limited thereto.

In one example of the present invention, it is confirmed that the maximal growth rate (maximal amount of microbial cells) of the mutant strain, Ajou_CEM45 (KCTC 12683BP), of the present invention is far higher than that of the control group; the absolute quantitative value of beta-carotene is 300% higher than that of the control group; and the absolute quantitative value of lycopene is 30% higher than that of the control group. Therefore, it is confirmed that the mutant strain, Ajou_CEM45 (KCTC 12683BP), of the present invention is suitable as a carotenoid producing strain due to the combined effects of excellent maximal growth rate (an increase in microbial cells amount) and superior ability to produce carotenoids.

Further, the present invention provides a method for producing carotenoids, in which the method includes the steps of (a) culturing the mutant strain; and (b) isolating and purifying carotenoids from a culture of the mutant strain of the step (a).

In the present invention, "cultivation" means that microorganisms are grown and developed under the environmental conditions which are suitably and artificially controlled.

The mutant strain according to the present invention is capable of growing and developing in a conventional medium. The medium may include nutrients required for the cultured subject, i.e., a microorganism to be cultured, in order to cultivate a specific microorganism, and the medium may be a mixture including a substance added for a special purpose. The medium is also referred to as an incubator or a culture medium solution and is a concept including all of the natural medium, synthetic medium, and selective medium.

The medium used for culturing the mutant strain according to the present invention should meet the requirements of a specific strain in a proper manner while controlling the temperature, pH and the like in a conventional medium including an appropriate carbon source, nitrogen source, amino acid, vitamin, and the like. As the carbon source that can be used, a mixed sugar of glucose and xylose is used as a main carbon source, and a sugar and a carbohydrate such as sucrose, lactose, fructose, maltose, starch and cellulose, an oil such as a soybean oil, a sunflower oil, a castor oil, and a coconut oil, a fatty acid such as fat, palmitic acid, stearic acid, and linoleic acid, an alcohol such as glycerol and ethanol, and organic acids such as acetic acid are additionally included. These materials may be used individually or as a mixture. Nitrogen sources that can be used may include an inorganic nitrogen source such as ammonia, ammonium sulfate, ammonium chloride, ammonium acetate, ammonium phosphate, ammonium carbonate, and ammonium nitrate, amino acid such as glutamic acid, methionine, and glutamine, and an organic substance such as peptone, NZ-amine, a meat extract, a yeast extract, a malt extract, a corn steep liquor, casein hydrolyzate, fish or decomposition products thereof, defatted soybean cake or decomposition products thereof. These nitrogen sources may be used alone or in combination. The medium may include potassium (I) phosphate, potassium (II) phosphate, and the corresponding sodium-containing salts as a phosphate source. The phosphate source which may be used includes potassium dihydrogen phosphate or dipotassium hydrogen phosphate or the corresponding sodium-containing salts. Sodium chloride, calcium chloride, iron chloride, magnesium sulfate, iron sulfate, manganese sulfate, calcium carbonate, and the like may be used as the inorganic compound. Finally, essential growth materials such as amino acids and vitamins can be used in addition to these materials.

In addition, suitable precursors may be used in the culture medium. The raw materials may be added to the culture in the process of the culture by an appropriate method such as a batch process, a fed-batch process, and a continuous process, but the present invention is not particularly limited thereto. Basic compounds such as sodium hydroxide, potassium hydroxide, and ammonia, or acid compounds such as phosphoric acid and sulfuric acid can be used in a suitable manner to adjust pH of the culture.

In the present invention, the method of isolating and purifying carotenoids from the mutant strain culture of the step (b) may be carried out by a suitable well-known method depending on the physicochemical properties of the corresponding substance. For example, distillation, electrodialysis, pervaporation, chromatography, solvent extraction, extraction by the reaction, high-pressure liquid chromatography (HPLC), and the like may be used, and they may be used in combination, but the present invention is not limited thereto.

Hereinafter, Examples are only for explaining the present invention in more detail, and thus it will be apparent to those skilled in the art that the scope of the present invention is not limited by these Examples in accordance with the concept of the present invention.

Example 1. Selection of Gene for Enzyme which is Involved in Carotenoid Biosynthesis and Production of Recombinant Vector In order to select a gene for an enzyme which is involved in the carotenoid biosynthesis and prepare a recombinant vector which is involved in the carotenoid biosynthesis, the following experiment was conducted.

More specifically, a genomic DNA of *Pantoea agglomerans* was extracted from *Pantoea agglomerans* in order to isolate and amplify clusters of the CrtE gene encoding geranylgeranyl pyrophosphate synthase, the CrtB gene encoding phytoene synthase, the CrtI gene encoding a phytoene desaturase, the CrtY gene encoding lycopene beta cyclase, the CrtX gene encoding glucosyl transferase, and a CrtZ gene encoding beta-carotene hydroxylase, which are enzymes that are involved in $C_{40}$ carotenoid biosynthesis.

Further, forward and reverse primers used for polymerase chain reaction were prepared in order to amplify the six genes. The primers were prepared through comparison and analysis in NCBI (http://www.ncbi.nlm.nih.gov/) which discloses the nucleotide sequence information of the six genes. Respective nucleotide sequences of the forward and reverse primers used for the amplification of the six genes and the types of the restriction enzymes included in the primers are listed in Table 1 below.

CrtE, CrtB, CrtI, CrtY, CrtX, and CrtZ gene clusters were amplified using a genomic DNA template of *Pantoea agglomerans* and primer pairs according to each gene. The amplified gene fragments were treated with EcoRI and XbaI, respectively, restriction enzymes, and inserted into pUC19 vector cleaved with the same enzyme to prepare the plasmid pUC19_CrtEXYIBZ. The vector map of the recombinant plasmid is illustrated in FIG. 2.

Figure 3:
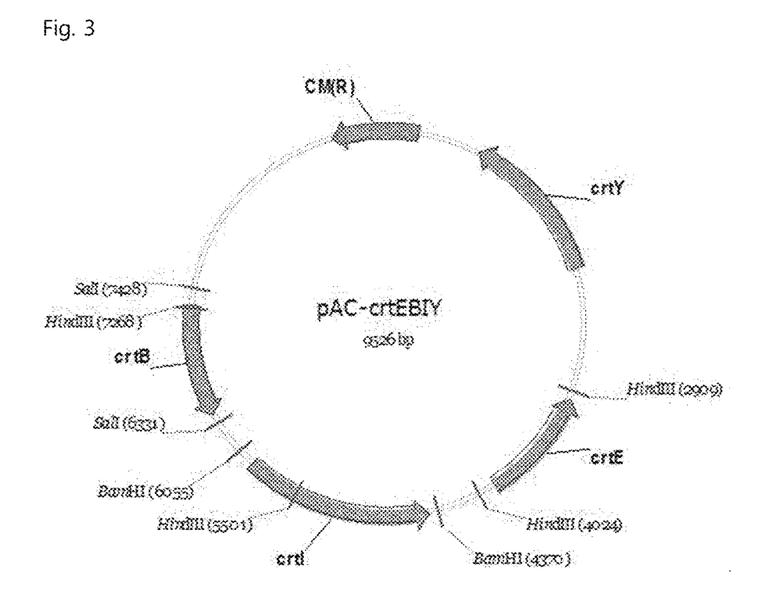
FIG. 3 is a diagram illustrating a vector map of pACM_CrtE_CrtB_CrtI_CrtY of the present invention.

Further, in order to express only the gene encoding the enzyme involved in the biosynthesis of beta-carotene, which is a kind of carotenoid, respective genes of CrtE, CrtB, CrtI, and CrtY were amplified and then the amplified genes fragments were treated with EcoRI and XbaI and then were inserted into the pUC_mod vectors cleaved with the same enzymes (Kim et al, 76 (15), 5199-5206, 2010) to prepare pUCM_CrtE, pUCM_CrtB, pUCM_CrtI, and pUCM_CrtY. Thereafter, it was amplified using a primer and a DNA template including the genes of pUCM_CrtE, pUCM_CrtB, pUCM_CrtI, and pUCM_CrtY plasmids, lac promoter, and terminator; then was treated with HindIII, SalI, BamHI, and XmnI; and was inserted into the plasmid pAC_mod which was cleaved with the same enzyme, thereby preparing the plasmid pACM_CrtE_CrtB_CrtI_CrtY. The vector map of the recombinant plasmid is illustrated in FIG. 3.

Figure 4:
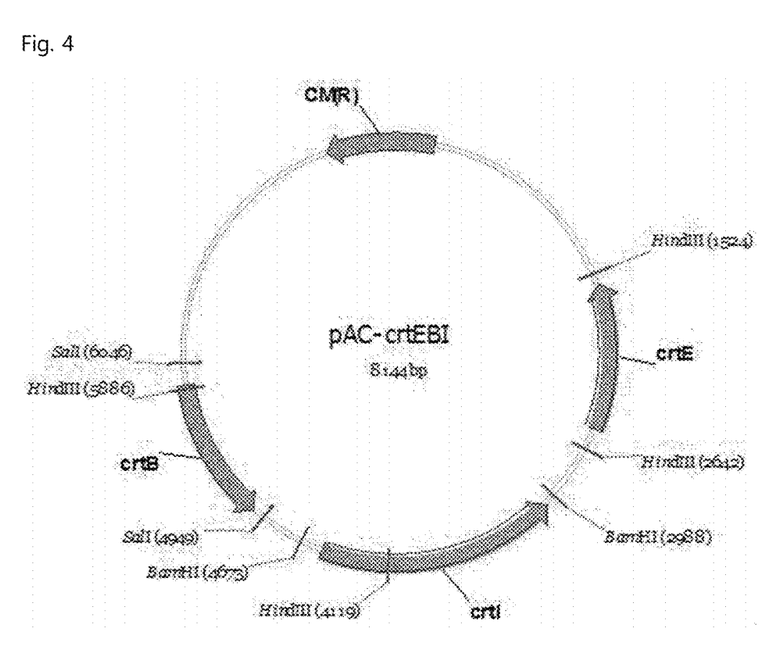
FIG. 4 is a diagram illustrating a vector map of pACM_CrtE_CrtB_CrtI of the present invention.

Further, in order to express the gene encoding the enzyme involved in the biosynthesis of lycopene, which is a kind of carotenoid, respective genes of CrtE, CrtB, and CrtI were amplified and then the amplified gene fragments were treated with EcoRI and XbaI and then were inserted into the pUC_mod vector cleaved with the same enzymes (Kim et al, 76 (15), 5199-5206, 2010) to prepare pUCM_CrtE, pUCM_CrtB, and pUCM_CrtI. Thereafter, it was amplified using a primer and a DNA template including the genes of pUCM_CrtE, pUCM_CrtB, and pUCM_CrtI plasmids, lac promoter, and terminator; then was treated with HindIII, SaiI, and BamHI; and was inserted into the plasmid pAC_mod which was cleaved with the same enzyme, thereby preparing the plasmid pACM_CrtE_CrtB_CrtI. The vector map of the recombinant plasmid is illustrated in FIG. 4.

TABLE 1

| Strain | gene | vector | Direction | Nucleotide sequence | Restriction enzyme |
|---|---|---|---|---|---|
| Pantoea agglomerans | CrtE | pUC19 | forward | 7 | XbaI |
| | CrtB | | | | |
| | CrtI | | | | |
| | CrtY | | | | |
| | CrtX | | | | |
| | CrtZ | | | | |
| | | | reverse | 8 | EcoRI |
| | CrtE | pAC_mod | forward | 9 | HindIII |
| | | | reverse | 10 | HindIII |
| | CrtB | | forward | 11 | SalI |
| | | | reverse | 12 | SalI |
| | CrtI | | forward | 13 | BamHI |
| | | | reverse | 14 | BamHI |
| | CrtY | | fonvard | 15 | XmnI |
| | | | reverse | 16 | XmnI |
| | CrtE | pAC_mod | forward | 9 | HindIII |
| | | | reverse | 10 | HindIII |
| | CrtB | | forward | 11 | SalI |
| | | | reverse | 12 | SalI |
| | CrtI | | forward | 13 | BamHI |
| | | | reverse | 14 | BamHI |

Example 2: Production of Mutant Strain and Comparison of its Carotenoid Productivity

*Escherichia coli* transformed with a recombinant vector including a gene encoding a carotenoid biosynthesis-related enzyme was irradiated to result in mutation, thereby producing a mutant strain. The following experiment was conducted in order to compare the productivity of the mutant carotenoid with that of the control group.

More specifically, in order to prepare a mutant strain, the plasmid pUC19_CrtEXYIBZ prepared in Example 1 was introduced into *Escherichia coli* and transformed. Thereafter, the recombinant *Escherichia coli* was cultured at 5 ml LB, 37° C., and 250 rpm for 14 hours and then was irradiated with $^{60}$Co of gamma-ray sources at an intensity of 0.3, 0.5, 1.0, 1.5, and 2.0 kGy/30 min to result in the mutation. The transformed mutant strains were diluted to a certain concentration and smeared in a solid LB medium (5 g/L of yeast extract, 5 g/L of sodium chloride (NaCl), 10 g/L of tryptone, and 15 g/L of agar powder) including 100 μg/ml ampicillin. Thereafter, a mutant strain in which the color concentration is enhanced based on yellow, an intrinsic expression color of beta-carotene which is one kind of carotenoid, is firstly selected. A single colony of the selected mutant strain was inoculated on 5 ml of an LB medium (5 g/L of yeast extract, 5 g/L of sodium chloride (NaCl), and 10 g/L of tryptone) including 100 μg/ml of ampicillin and was shake cultured at 37° C. for 16 hours. Each 5 ml of the culture solution obtained was centrifuged and subjected to secondary selecting based on the intensity of yellow color expressed in the obtained microbial cells. The finally selected mutant strain was named "Ajou_CEM45", which was deposited on Sep. 23, 2014 with Microorganism Resource Center, Korea Research Institute of Bioscience and Biotechnology in Korea, and its accession number is KCTC 12683BP.

A single colony of Ajou_CEM45, the transformed mutant strain, was inoculated to 5 ml of LB medium (5 g/L of yeast extract, 5 g/L of sodium chloride (NaCl), and 10 g/L of tryptone) including 100 μg/ml of ampicillin or 50 μg/ml of chloramphenicol and was shake cultured at 37° C. for 16 hours. Each 5 ml of the obtained culture was inoculated to 100 ml of TB medium (24 g/ml of yeast extract, 12 g/L of tryptone, 5.03 g/L of glycerol, 2.31 g/L of monopotassium phosphate ($KH_2PO_4$), and 12.59 g/L of dipotassium phosphate ($K_2HPO_4$)), and then was shake cultured at 30° C. for 60 hours. Then, 1 ml of each culture was selected, and each absorbance thereof was measured using a spectrophotometer at a wavelength of 600 nm. Then, the amount of microbial cells was determined by multiplying by the dilution factor (See Table 2, FIG. 5, and FIG. 6). Further, each 5 ml of the cultured medium was centrifuged to obtain microbial cells, and the microbial cells were dissolved with 10 ml of 100% acetone to extract the expressed carotenoids. 10 ml of hexane and water ($H_2O$) divided carotenoid layers, and then the carotenoids were isolated. The isolated carotenoids were transferred to a glass test tube and then dried using a high-pressure dryer for 30 minutes. The dried carotenoid extract was dissolved in 1 ml of ethyl acetate, and then the carotenoid in 10 μl of the extract was measured using high-pressure liquid chromatography with photodiode array detector (HPLC-PAD).

Beta-carotene and lycopene was quantitated by substituting the equation obtained from the calibration curve, and the amount of carotenoid was calculated by calculating the dilution rate. Here, to generate a calibration curve, standard beta-carotene and lycopene (Sigma) were purchased and dissolved in ethyl acetate, and then diluted with ethyl acetate at different concentrations, and the amount of beta-carotene was measured using high-pressure liquid chromatography-photometric array detector (Agilent Technologies 1200 series model in which a sample inserting device (auto-sampler) is mounted), thereby using them to prepare the standard calibration curve. Specifically, Agilent Zorbax SB-C18 (4.6×150 mm, 5-micron) was used as a column, and the mobile phase was obtained under a condition of acetonitrile: 80/methanol: 15/isoprepanol 5 (v/v %) at 1.0 ml/min, 23° C. of the column temperature using a diode array detector (DAD) as a measuring instrument. The amount of injected sample was 10 μl, and detection was performed using a spectrometry method (190 nm to 900 nm). XL1-Blue strain was used as a control group. The microbial cells of Ajou_CEM45 (KCTC 12683BP), the mutant strain of the present invention and the yield of each carotenoid, confirmed by the method, are listed in Table 2 below. Further, productions of beta-carotene and strain growth are illustrated in FIG. 5, and productions of lycopene and strain growth are illustrated in FIG. 6.

TABLE 2

|  | Beta-carotene | | Lycopene | |
| --- | --- | --- | --- | --- |
|  | Maximal growth rate ($OD_{600}$) | Absolute quantitative value (mg/L) | Maximal growth rate ($OD_{600}$) | Absolute quantitative value (mg/L) |
| XL1-Blue (control group) | 12 | 55 | 9 | 6.96 |
| Ajou_CEM45 (KCTC 12683BP) | 17 | 169 | 17 | 9.18 |

Figure 5:
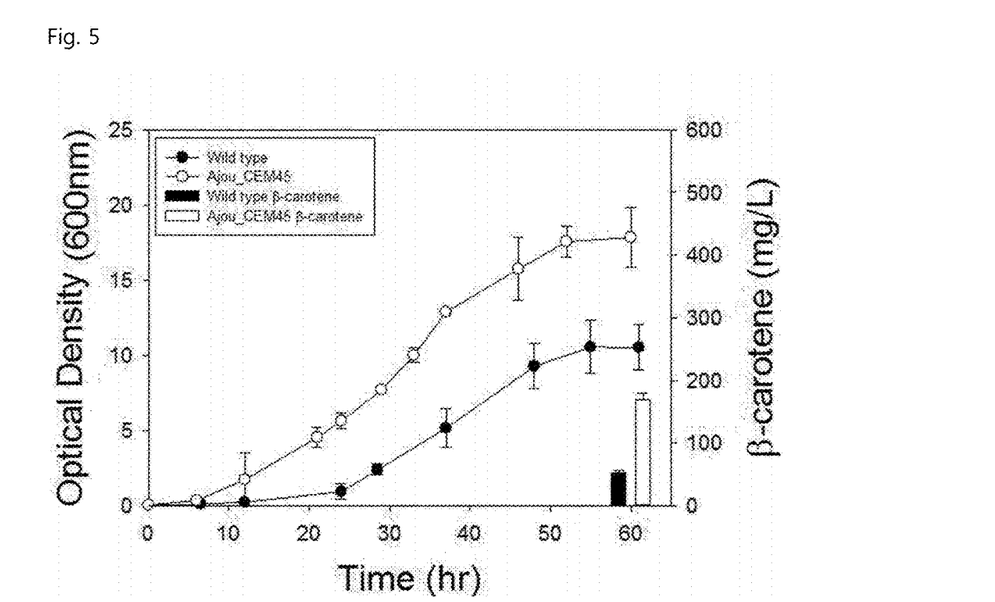
FIG. 5 illustrates the production and strain growth of beta-carotene by a control group and Ajou_CEM45 (KCTC 12683BP), the mutant strain of the present invention.
Figure 6:
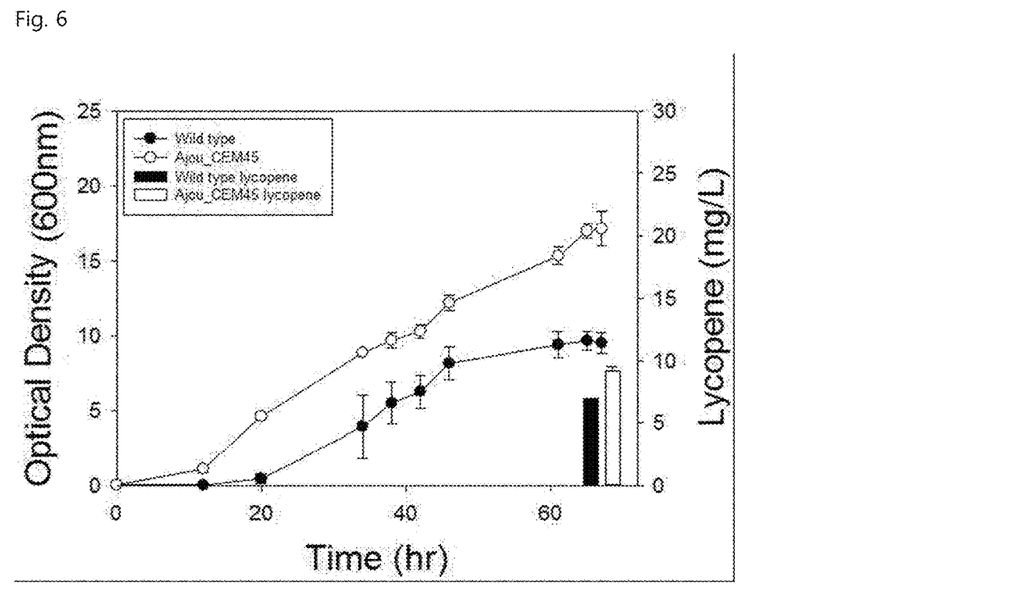
FIG. 6 illustrates the production and strain growth of lycopene by a control group and Ajou_CEM45 (KCTC 12683BP), the mutant strain of the present invention.

As listed in Table 2 and illustrated in FIG. 5, as for Ajou_CEM45 (KCTC 12683BP), the mutant strain of the present invention, it was confirmed that the maximal growth rate (maximal amount of microbial cells) thereof was even higher than that of the control group and the absolute quantitative value of beta-carotene thereof was 300% higher than that of the control group, under the same amount of energy source.

Further, as listed in Table 2 and illustrated in FIG. 6, as for Ajou_CEM45 (KCTC 12683BP), the mutant strain of the present invention, it was confirmed that the maximal growth rate thereof was about twice as high as that of the control group, and that the absolute quantitative value of lycopene was 30% higher than that of the control group.

In order to re-verify the results, the expression levels of beta-carotene were observed in Ajou_CEM45 (KCTC 12683BP), the mutant strain of the present invention and the control group in which the plasmid pUC19_CrtEXYIBZ was introduced into the wild-type XL1-Blue strain. Thus, the results are illustrated in FIG. 7.

Figure 7:
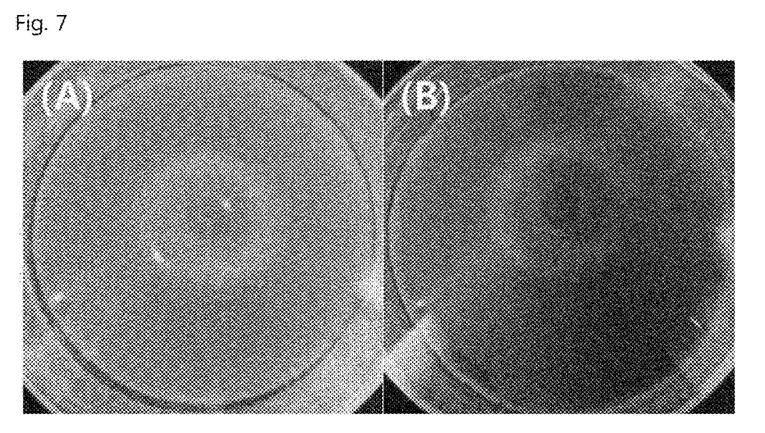
FIG. 7A is an image illustrating the changes in the colors of respective microbial cells according to the expression of beta-carotene in the XL1-Blue control group into which the plasmid pUC19_CrtEXYIBZ was introduced.
FIG. 7B is an image illustrating the changes in the colors of respective microbial cells according to the expression of beta-carotene in the mutant strain Ajou_CEM45 (KCTC 12683BP) of the present invention.

As illustrated in FIG. 7, Ajou_CEM45 (KCTC 12683BP), the mutant strain of the present invention, was confirmed to exhibit remarkably excellent ability to produce carotenoids as compared with the control group.

Through the experiments as described above, Ajou_CEM45 (KCTC 12683BP), the mutant strain of the present invention, was confirmed to exhibit excellent maximal growth rate (an increase in microbial cells) and ability to produce carotenoids.

Example 3: Confirmation of Internal or External Changes of Mutant Strain

The following experiment was carried out in order to compare the internal or external changes of Ajou_CEM45 (KCTC 12683BP), the mutant strain, prepared in Example 2 with those of the control group.

More specifically, XL1-Blue, a wild-type *Escherichia coli*, was transformed by introducing the plasmid pUC19_CrtEXYIBZ prepared in Example 1 thereinto. A single colony of the XL1-Blue *Escherichia coli* into which the plasmid pUC19_CrtEXYIBZ was introduced and Ajou_CEM45 (KCTC 12683BP), the mutant strain, prepared in Example 2 was inoculated into 5 ml of an LB medium (5 g/L of yeast extract, 5 g/L of sodium chloride, and 10 g/L of tryptone) including 100 μg/ml of ampicillin, and then it was shake cultured at 37° C. for 16 hours. Each 5 ml of the obtained culture was inoculated into 50 ml of TB medium (24 g/ml of yeast extract, 12 g/L of tryptone, 5.03 g/L of glycerol, 2.31 g/L of monopotassium phosphate ($KH_2PO_4$), and 12.59 g/L of dipotassium phosphate ($K_2HPO_4$)) including 100 μg/ml of ampicillin, and then it was shake cultured at 30° C. Subsequently, 1 ml of each of the microbial cells was collected during the lag phase of the microbial cell growth and was subject to centrifugation so that only microbial cells were isolated. Then, the microbial cells were immobilized using 2 ml of Karnovsky's mixture at 4° C. for 2 hours, followed by washing with 0.05 M sodium cacodylate buffer for 10 minutes three times. Secondary immobilization was carried out with a mixture of 2% osmium tetroxide and 0.1M sodium cacodylate at 4° C. for 2 hours. After a wash with water, en-bloc staining was carried out with 0.5% uranyl acetate for 30 minutes.

The dehydrogenation was carried out sequentially using various concentrations of ethanol (for example, 30%, 50%, 70%, 80%, 90%, and 100%), and the process was repeated three times. Then, the microbial cells were dissolved with hexamethyldisilazane and reacted for 10 minutes. After drying, sizes and lengths of Ajou_CEM45 (KCTC 12683BP), the mutant strain of the present invention and the control group were measured using supra 55 vp scanning electron microscopy (SEM).

After the dehydrogenation with ethanol, the microbial cells reacted with propylene oxide for 10 minutes. Then, the microbial cells were filled with Spurr's resin (4.1 g of ERL 4221, 1.43 g of D.E.R. 736, 5.9 g of NSA, and 0.1 g of DMAE) and then stirred and reacted for one day. After centrifugation, only the microbial cells were isolated and re-filled with Spurr's resin (4.1 g of ERL 4221, 1.43 g of D.E.R. 736, 5.9 g of NSA, and 0.1 g of DMAE) and then were dried at 70° C. Then, sizes and thicknesses of cell membranes of the control group and Ajou_CEM45 were measured using JEM1010 transmission electron microscope (TEM).

Figure 8:
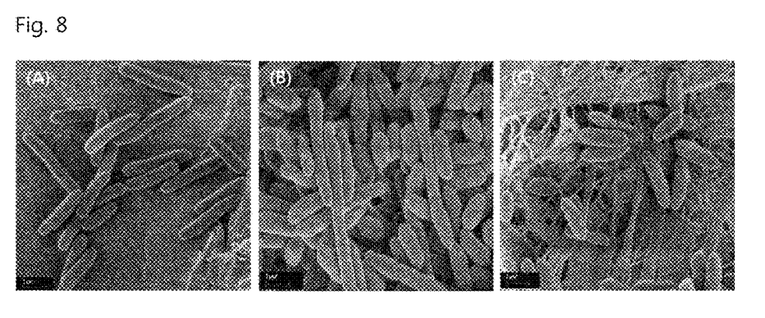
FIG. 8 is images illustrating the result of observing the size and length difference of respective microbial cells using a scanning electron microscopy (SEM).
Figure 9:
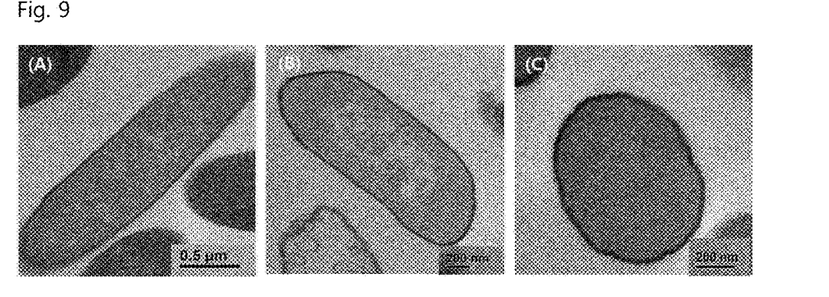
FIG. 9 is images illustrating the result of observing the cell membrane size and thickness difference of respective microbial cells using a transmission electron microscopy (TEM).

Table 3 lists a result of comparison of the average microbial cell lengths of Ajou_CEM45 (KCTC 12683BP), the mutant strain of the present invention and a recombinant *Escherichia coli* XL1-Blue having the ability to produce $C_{40}$ carotenoids and a recombinant *Escherichia coli* XL1-Blue into which the plasmid pUC19 was introduced as a control group. Further, FIG. 8 illustrates the difference in the size and length of Ajou_CEM45 (KCTC 12683BP) of the present invention and the control group, identified using SEM. FIG. 9 illustrates the difference in cell membrane size and thickness of the control group and Ajou_CEM45 (KCTC 12683BP) using TEM.

TABLE 3

| | Average length of microbial cell (μm) |
|---|---|
| XL1-Blue(A) | 2.8 ± 0.9 |
| pUC19_CrtEXYIBZ-introduced plasmid XL1-Blue(B) | 3.8 ± 2.7 |
| Ajou_CEM4 (KCTC 12683BP) | 1.7 ± 0.5 |

As listed in Table 3, illustrated in FIG. 8, and FIG. 9, Ajou_CEM45 (KCTC 12683BP), the mutant strain of the present invention, was confirmed to have a smaller cell size (i.e., shorter cell length) and a thicker cell membrane thickness than the control group. Therefore, the mutant strain of the present invention was morphologically/physiologically changed by irradiation, and the mutation completely proceeded.

DEPOSIT INFORMATION

Name of Depositary Institute: Korean Collection for Type Cultures (formerly Microorganism Resource Center) of Korea Research Institute of Bioscience and Biotechnology located in at 125 Gwahak-ro, Yuseong-gu, Dajeon 305-806, Republic of Korea
Accession number; KCTC12683BP
Deposit date: Sep. 23, 2014

The invention claimed is:

1. A mutant strain *Escherichia coli* whose accession number is KCTC 12683BP having an ability to over-produce a carotenoid, which is mutagenized by $^{60}$Co gamma-ray source irradiation, wherein the mutant strain includes a CrtE gene which encodes geranylgeranyl pyrophosphate synthase and consists of the nucleotide sequence set forth in SEQ ID NO: 1; a CrtB gene which encodes phytoene synthase and consists of the nucleotide sequence set forth in SEQ ID NO: 2; a CrtI gene which encodes phytoene desaturase and consists of the nucleotide sequence set forth in SEQ ID NO: 3; a CrtY gene which encodes lycopene beta cyclase and consists of the nucleotide sequence set forth in SEQ ID NO: 4; a CrtX gene which encodes glucosyl transferase and consists of the nucleotide sequence set forth in SEQ ID NO: 5; and a CrtZ gene which encodes beta-carotene hydroxylase and consists of the nucleotide sequence set forth in SEQ ID NO: 6, and is transformed with a recombinant vector for production of a carotenoid.

2. The mutant strain of claim 1, wherein the CrtE gene, the CrtB gene, the CrtI gene, the CrtY gene, the CrtX gene, and the CrtZ gene are isolated from *Pantoea agglomerans*.

3. The mutant strain of claim 1, wherein the recombinant vector for production of a carotenoid is illustrated in FIG. 2.

4. The mutant strain of claim 1, wherein the carotenoid includes one or more kinds selected from the group consisting of phytoene, neurosporene, b-carotene, lycopene, zeaxanthin, torulene, chlorobactene, flexixanthin, g-carotene, 4-keto-g-carotene, myxol, astaxanthin, isorenieratene, canthaxanthin, and nostoxanthin.

5. A method for producing a carotenoid, the method comprising the steps of:
(a) culturing the mutant strain of claim 1; and
(b) isolating and purifying the carotenoid from a culture of the mutant strain of the step (a).

* * * * *

SEQUENCE LISTING

<160> NUMBER OF SEQ ID NOS: 16

<210> SEQ ID NO 1
<211> LENGTH: 912
<212> TYPE: DNA
<213> ORGANISM: Artificial Sequence
<220> FEATURE:
<223> OTHER INFORMATION: CrtE(Geranylgeranyl pyrophosphate synthase) gene

<400> SEQUENCE: 1

```
atgatgacgg tctgtgcaga acaacacgtc aatttcatac acagcgatgc agccagcctg        60
ttgaacgaca ttgagcaacg gctagatcag cttttaccgg ttgaaagcga acgtgactta       120
gtgggcgctg ccatgcgcga cggtgcgctg gcaccaggaa agcgtatccg tccactgctg       180
ttgttgctgg cagcgcgcga tctgggctgc aacgccacgt ctgccggcct gctcgatctc       240
gcctgcgcgg tagagatggt gcatgccgca tcactgattc tggatgacat gccctgcatg       300
gatgatgcgc aactgcgtcg cggacgtccg accattcatt gccagtatgg tgaacatgtc       360
gcgattctgg ccgcggtggc cctgctgagt aaggcattcg gcgtggttgc tgcggcagaa       420
ggcttaacgg caaccgccag agccgacgct gtggcagaat tatcccacgc agtcggcatg       480
caggggctgg tacaggggca gtttaaggat ctctccgaag gtgacaagcc acgcagcgct       540
gacgccattc tgatgaccaa tcactataaa accagcaccc tgttctgcgc ctccatgcag       600
atggcctcta tcgtggctga agcctcaggt gaagcccgcg aacagctgca ccgttttttcg       660 cttaatcttg gtcaggcttt ccagctactg gacgatctca ctgacggcat ggccgacaca       720
ggtaaagatg ctcatcagga tgacgggaaa tcaacgctgt gaatctgct ggggccacag       780 gcggttgaaa cgcgactgcg cgatcatctg cgctgcgcca gcgagcatct gttatcggcc       840
tgccaggacg gttatgccac acaccatttt gttcaggcct ggtttgagaa aaaactcgct       900
gccgtcagtt aa                                                           912
```

<210> SEQ ID NO 2
<211> LENGTH: 891
<212> TYPE: DNA
<213> ORGANISM: Artificial Sequence
<220> FEATURE:
<223> OTHER INFORMATION: CrtB(Phytoene synthase) gene

<400> SEQUENCE: 2

```
atggaggtgg gatcgaaaag ctttgccacc gcgtcaaaac tgtttgatgc caaaacccga        60
cgcagcgtgc tgatgctcta cgcttggtgc cgtcactgtg atgatgtgat tgacgatcag       120
gtcctgggat tcagcaacga tacgccatcg ctgcaatccg ccgaacagcg cctggcgcag       180
```

```
ctggagatga aaacgcgtca ggcctatgcc gggtcccaga tgtatgagcc cgcctttgcg    240
gcctttcagg aggtggcaat ggcacacgat attctgcctg cttacgcttt tgatcatctg    300
gcgggatttg cgatggacgt gcatgagaca cgctatcaga cgctggatga tacgctgcgt    360
tactgttacc acgtcgcggg cgtggttggc ctgatgatgg cgcagattat gggcgtacgc    420
gacaacgcca cgctggatcg cgcctgcgat ctcggtctgg cgtttcagct gaccaatatt    480
gcgcgcgata tcgttgaaga tgctgaagcg ggacgctgct atctgcccgc tgcgtggctg    540
gctgaagagg ggcgtacccg agagaatctc gccgatccgc aaaatcgtaa ggcattaagc    600
cgcgtcgccc gtcggctggt ggaaacggcg gagccctatt atcgatcggc gtcggctggc    660
ctgccgggtt taccgctgcg ttcagcgtgg gcgattgcta ccgcgcagca ggtctatcgt    720
aaaatcggta tgaaggtggt tcaggcgggt tcacaggcgt gggagcaacg ccagtccacc    780
agcacgccag agaaactggc actgctggtg gcggcatcgg gtcaggcggt tacttcccgg    840
gtggcgcgtc acgctccacg ctccgctgat ctctggcagc gccccgttta a           891
```

<210> SEQ ID NO 3
<211> LENGTH: 1479
<212> TYPE: DNA
<213> ORGANISM: Artificial Sequence
<220> FEATURE:
<223> OTHER INFORMATION: CrtI(Phytoene desaturase) gene

<400> SEQUENCE: 3

```
atgaatagaa ctacagtaat tggcgcaggc tttggtggtc tggctctggc aattcgcctt     60
caggcgtcag gcgttcccac ccgactgctg gagcagcgtg acaagcctgg cggccgggct    120
tatgtctatc aggatcaggg cttcacgttt gatgccggcc ccacggtaat caccgatccc    180
agcgccattg aagagctgtt caccctcgcg ggtaaaaagc tctctgacta tgtcgagctg    240
atgccggtga agccgtttta tcgcctctgc tgggagtccg gcaaggtgtt cagttatgac    300
aacgatcagc ccgcgctgga agcgcagatt gccgcgttta tccgcgtgac gttaaggga    360 tatcgtcgct ttctggccta tcccgagcg tgtttgctg aaggctattt gaagcttggc    420
accgtgccgt ttctgtcatt ccgcgatatg ctgcgggccg cacctcagct ggcaaaactt    480
caggcatggc gcagcgttta cagcaaagtg gcgagctaca ttgaagatga gcatctgcgt    540
caggccttct ctttccactc actgctggtg gcggaaaatc cgtttgccac ttcctcaatc    600
tataccctga ttcatgcgct ggaacgtgaa tggggcgtct ggttcccgcg cggtggcacg    660
ggcgcgctgg tgcagggcat ggtgaaactg tttgaagatc tggcggcga agtggagctc    720 aatgccagcg ttgcccggct ggagacccag gaaaacggaa ttaccgcggt acacctgaaa    780
gatgccgggg tcttcccaac ccgcgcggtt gcctccaacg cagatgtggt tcacacctac    840
cgcgaactgc tgagccagca tcccgcttcg caggcgcagg acgatcact gcaaaacaaa    900 cgcatgagca actcactgtt tgtgatctat tttggcctga tcatcatca cgatcagctg    960 gcgcaccaca cggtctgctt tggtccgcgc tatcgtgagt tgattgatga gatctttaac   1020
aaagatggcc tggcagagga cttctcgctc tatctgcatg cgccctgcgt gaccgatccc   1080
tcactggcac cggaaggctg cggcagctac tacgtgctgg cgccggttcc gcacctcggc   1140
accgccgata tcgactgggc cgttgaaggt ccgcgcctgc gcgatcgcat tttcgactat   1200
ctggaacagc attacatgcc gggcctgcgt agccagttgg tcacgcatcg catcttcacg   1260
ccgtttgatt ccgcgatga gctgaatgcg tatcagggct cggccttctc ggtggagccg   1320
atcctgacgc aaagcgcctg gttccggcct cataaccgcg ataaaaatat taataatctc   1380
```

| | |
|---|---|
| tatctggtcg gtgctggtac ccatcctggc gcgggtattc caggcgttat tggctcggcc | 1440 |
| aaggctactg caggattgat gctggaggat ctggcttga | 1479 |

<210> SEQ ID NO 4
<211> LENGTH: 1161
<212> TYPE: DNA
<213> ORGANISM: Artificial Sequence
<220> FEATURE:
<223> OTHER INFORMATION: CrtY(Lycopene cyclase) gene

<400> SEQUENCE: 4

| | |
|---|---|
| atgccgcggt atgatctgat tctggtgggt gcgggactgg ccaacgggct gatcgccctg | 60 |
| cgcctgagac agcagcggcc ctccctgcgc attctgctga ttgacgccga acgtgaaccg | 120 |
| ggtgccaatc atacctggtc gtttcatgcg aagatctca ccgaaacgca gcatcgctgg | 180 |
| atcgctccgc tggtagtaca tcactggcct ggctatgagg tccgcttttcc ccaacgcagt | 240 |
| cgcagtctga cagtggcta ttttgcgtg actgcggagc gcttcgcgca ggtcatccgc | 300 |
| gacaggtttg cgccggatct gctgctgaat acccggggttg cgagcatcgc ttcacgcgcg | 360 |
| gttacgctgg acgatggccg ggtgctggag agtgacgcag tgattgatgg ccgtggctac | 420 |
| cagcccgatg ccgcgctgcg catgggcttc cagtcgtttg tcggacagga gtggcagctc | 480 |
| agcgagccac atggcctgac cgcgccgatc atcatggatg ccacggtaga tcagcaggca | 540 |
| ggctatcgct ttgtctacag cctgcccttt tctgcagaca ccctgctgat tgaagatacc | 600 |
| cattacattg ataacgccac gctggaaggc gatcgcgccc gtcagaatat ccgcgcctat | 660 |
| gccgcgcagc aggggtggcg tttagaccgg ctgctacgcg aagagcaagg cgaattaccc | 720 |
| attacgctga ccggcgacgt ggccgccttc tggcagaacc gcgatttgcc ctgcagcggt | 780 |
| ttgcgtgccg ggttattcca tccgactacc ggctattctc tgccgctggc ggttgctctg | 840 |
| gctgaccggc tggcgcagat gcagacgttt acctctgaga ccctgcacgc caccattcag | 900 |
| caattcgcca gtcaggcatg gcagcaacag cgcttcttcc gcatgctgaa ccgtatgttg | 960 |
| tttctggcgg tccggctga ccagcgctgg caggttatgc aacgtttta cggccttccc | 1020 |
| gaaggtctga tcgcccgttt ttatgcggga aaactcactt tgcctgatcg gctgcgcatc | 1080 |
| ttaagcggca gccccccggt ccccgttctg gcggcgttac aggctattat gactcctcac | 1140 |
| cgtcaacagg cgatgcaatg a | 1161 |

<210> SEQ ID NO 5
<211> LENGTH: 1296
<212> TYPE: DNA
<213> ORGANISM: Artificial Sequence
<220> FEATURE:
<223> OTHER INFORMATION: CrtX(Zeaxanthin glucosyltransferase) gene

<400> SEQUENCE: 5

| | |
|---|---|
| atgagccact tgcggtcat tgcaccgcct ttctatagcc atgtgcaggc gcttcagcat | 60 |
| cttagccagg ccttaatcgc acgcggacac cagatcactt tcatccagca gacggacgtt | 120 |
| ggcgcgctac tcaccgatag ccggatcggc ttttttcccgc tgggtttagc ctcgcatccg | 180 |
| gcgggcagtc tggcacacac cctgcaactg gcggcgcatc tctcggccc tcaatgctg | 240 |
| aaactgatca atgagatggc ccgcagcacc gatatgctct gtcgtgaact gcccgtggtg | 300 |
| ctgagcacgc tggcgattga tggcgtgatc gtcgatcaga tggagcctgc cggtgcactg | 360 |
| gcggcagaag cgctgaacct gccttatgtt tcggttgcct gtgcgctgcc acttaaccgt | 420 |

```
gaagcggatt tcccgctggc cgtgatgccg tttgactatg ccagaaccga tcaggcgcgc     480
gaacgctatc gcaccagtga aaaaatctat gactggctga tgcgacgtca cgatcgggtg     540
atcgcccgca acgctcatgc gatgggatta gcaccacggg aaaaactgca tcactgtttt     600
tcaccgctgg cgcagatcag ccagctgatt ccggaactgg attttccccg ccagacgctg     660
cccgatcatt tccattcggt tggcccgctg cgtaccactg aaccggcacc cgccgcatct     720
cagcctcgct actttccgca tggcgacaga ccgcgcattt ttgcttcact cggcacgctg     780
cagggacatc gctacggcct gtttaaaacc atcgtccgcg cctgccagga gatcgatgct     840
cagttattgc tggcgcattg cggtcggttg tcacctttcc aggcggagaa actggcgcag     900
gccagccatg ttcaggtggt cgattttgcc gaccaggcgg ctgcactggc gcaggccgat     960
cttgtcatta cgcacggcgg catgaatacg gtgctggatg ggattaacca cctgacgccg    1020
ctgctgacga tcccgctggc ctttgatcag ccgggtgtgg ctgccagagt ggtctggcac    1080
ggtatcggac gtcgcgcctc acgctttacc accagccact ccatggcacg tcagctccag    1140
accttactgg ctgatgaaag ctacgttcag cagatgaaaa cgctgcgtag cgcacttcgt    1200
caggcgggcg gaaccaccct ggcggcggac atcgtcgaac aggcgatgct gacccgccag    1260
ccggtgctca ccaggagaca ctatgccgcg gtatga                              1296

<210> SEQ ID NO 6
<211> LENGTH: 527
<212> TYPE: DNA
<213> ORGANISM: Artificial Sequence
<220> FEATURE:
<223> OTHER INFORMATION: CrtZ(Beta carotene hydroxylase) gene

<400> SEQUENCE: 6
atgttgtgga tttggaatgc cctgattgtt ctggtcactg ttatcggaat ggagataacg      60
gctgcactgg cgcacagata cattatgcat ggctggggtt ggggctggca tctgtcacat     120
catgaaccgc ataaaggctg gtttgaggtt aatgacctct atgccgtagt gttcgccgct     180
ctgtcgattt tgctcatttta tctgggcagc acgggtgtct ggcccttgca gtggatcggc     240
gcagtatgac gctctacggc ctgctctatt ttattgtgca tgacggcctg gtgcatcagc     300
gctggccatt ccgctatgtt ccgcgccggg gttatttacg caggctttat atggcgcacc     360
gcatgcatca tgcggtacga ggcaaagagg gctgtgtctc gtttggcttt ctttacgcgc     420
cgccgctgtc aaaactgcag gcgacgctgc gagaacgtca tggcgttaaa cggggcgctg     480
ccagagatca gcggagcgtg gagcgtgacg cgccacccgg aagtaa                    527

<210> SEQ ID NO 7
<211> LENGTH: 41
<212> TYPE: DNA
<213> ORGANISM: Artificial Sequence
<220> FEATURE:
<223> OTHER INFORMATION: forward primer specific for crtEBIYXZ cluster

<400> SEQUENCE: 7
gctctagaag gaggattaca aaatgatgac ggtctgtgca g                          41

<210> SEQ ID NO 8
<211> LENGTH: 29
<212> TYPE: DNA
<213> ORGANISM: Artificial Sequence
<220> FEATURE:
<223> OTHER INFORMATION: reverse primer specific for crtEBIYXZ cluster

<400> SEQUENCE: 8
```

```
ccggaattca tgttgtggat ttggaatgc                                           29
```

<210> SEQ ID NO 9
<211> LENGTH: 23
<212> TYPE: DNA
<213> ORGANISM: Artificial Sequence
<220> FEATURE:
<223> OTHER INFORMATION: forward primer specific for CrtE at the
      pAC-crtEBIY

<400> SEQUENCE: 9

```
cccaagcttc cgactggaaa gcg                                                 23
```

<210> SEQ ID NO 10
<211> LENGTH: 24
<212> TYPE: DNA
<213> ORGANISM: Artificial Sequence
<220> FEATURE:
<223> OTHER INFORMATION: reverse primer specific for CrtE at the
      pAC-crtEBIY

<400> SEQUENCE: 10

```
cccaagcttc ggtgtgaaat accg                                                24
```

<210> SEQ ID NO 11
<211> LENGTH: 24
<212> TYPE: DNA
<213> ORGANISM: Artificial Sequence
<220> FEATURE:
<223> OTHER INFORMATION: forward primer specific for CrtB at the
      pAC-crtEBIY

<400> SEQUENCE: 11

```
acgcgtcgac ccgactggaa agcg                                                24
```

<210> SEQ ID NO 12
<211> LENGTH: 25
<212> TYPE: DNA
<213> ORGANISM: Artificial Sequence
<220> FEATURE:
<223> OTHER INFORMATION: reverse primer specific for CrtB at the
      pAC-crtEBIY

<400> SEQUENCE: 12

```
acgcgtcgac cggtgtgaaa taccg                                               25
```

<210> SEQ ID NO 13
<211> LENGTH: 22
<212> TYPE: DNA
<213> ORGANISM: Artificial Sequence
<220> FEATURE:
<223> OTHER INFORMATION: forward primer specific for CrtI at the
      pAC-crtEBIY

<400> SEQUENCE: 13

```
cgggatcccc gactggaaag cg                                                  22
```

<210> SEQ ID NO 14
<211> LENGTH: 23
<212> TYPE: DNA
<213> ORGANISM: Artificial Sequence
<220> FEATURE:
<223> OTHER INFORMATION: reverse primer specific for CrtI at the
      pAC-crtEBIY

<400> SEQUENCE: 14

```
cgggatcccg gtgtgaaata ccg                                              23

<210> SEQ ID NO 15
<211> LENGTH: 24
<212> TYPE: DNA
<213> ORGANISM: Artificial Sequence
<220> FEATURE:
<223> OTHER INFORMATION: forward primer specific for CrtY at the
      pAC-crtEBIY
<220> FEATURE:
<221> NAME/KEY: misc_feature
<222> LOCATION: (4)..(7)
<223> OTHER INFORMATION: a, c, g, or t

<400> SEQUENCE: 15
gaannnnttc ccgactggaa agcg                                             24

<210> SEQ ID NO 16
<211> LENGTH: 25
<212> TYPE: DNA
<213> ORGANISM: Artificial Sequence
<220> FEATURE:
<223> OTHER INFORMATION: reverse primer specific for CrtY at the
      pAC-crtEBIY
<220> FEATURE:
<221> NAME/KEY: misc_feature
<222> LOCATION: (4)..(7)
<223> OTHER INFORMATION: a, c, g, or t

<400> SEQUENCE: 16
gaannnnttc cggtgtgaaa taccg                                            25
```